United States Patent [19]

Lescouzeres et al.

[11] Patent Number: 5,786,608

[45] Date of Patent: Jul. 28, 1998

[54] SEMICONDUCTOR CHEMICAL SENSOR DEVICE WITH SPECIFIC HEATER STRUCTURE

[75] Inventors: Lionel Lescouzeres, Toulouse; Alain Seube, Plaisance; Anne-Marie Gue, Rebigue, all of France

[73] Assignee: Motorola, Inc., Schaumburg, Ill.

[21] Appl. No.: 806,816

[22] Filed: Feb. 26, 1997

[30] Foreign Application Priority Data

Mar. 14, 1996 [FR] France .................. 96 03216

[51] Int. Cl.$^6$ .................. H01L 23/58; G01N 7/00; H01C 7/00
[52] U.S. Cl. .................. 257/253; 73/31.06; 338/34
[58] Field of Search .................. 257/252, 253, 257/414; 73/31.06, 23.4, 25.05; 338/34

[56] References Cited

U.S. PATENT DOCUMENTS

| | | | |
|---|---|---|---|
| 4,343,768 | 8/1982 | Kimura | 422/97 |
| 4,580,439 | 4/1986 | Manaka | 73/23 |
| 4,967,589 | 11/1990 | Yagawara et al. | 73/23.25 |
| 5,147,523 | 9/1992 | Yagawara et al. | 204/424 |
| 5,250,170 | 10/1993 | Yagawara et al. | 204/431 |
| 5,652,443 | 7/1997 | Kasai | 257/252 |

*Primary Examiner*—David B. Hardy
*Attorney, Agent, or Firm*—Rennie William Dover

[57] ABSTRACT

A semiconductor device (50) comprises a semiconductor base, a heater (20) formed over the semiconductor base from conductive material, such as polysilicon, and a layer (22) for heating by the heater. The heater (20) comprises first (24) and second (26) arms extending over the semiconductor base from a heater portion (28) and an opening (34) extending vertically through the heater portion (28). A first heater contact (30) is coupled to an end of the first arm (24) and a second heater contact (32) is coupled to an end of the second arm (26). The layer (22) is formed over the opening (34) and heater portion (28) such that a vertical axis through the center (36) of the opening (34) extends through the center (36) of the layer (22).

22 Claims, 2 Drawing Sheets

—PRIOR ART—

5,786,608

SEMICONDUCTOR CHEMICAL SENSOR DEVICE WITH SPECIFIC HEATER STRUCTURE

FIELD OF THE INVENTION

This invention relates to a semiconductor device and a method of forming a semiconductor device. More particularly, this invention relates to a semiconductor chemical sensor device and a method of forming a semiconductor chemical sensor device.

BACKGROUND OF THE INVENTION

A chemical sensor is a device which monitors the concentration of a given chemical species in a liquid or a gas. Chemical sensors are used, for example, to detect unsafe levels of poisonous or explosive gases in the work and home environments.

Chemical sensors formed using hybrid technology, such as for example sensors formed on ceramic substrates, are well known. It is also known to fabricate a semiconductor chemical sensor on a semiconductor substrate. This invention is concerned with semiconductor chemical sensors.

Typically chemical sensors comprise a sensitive layer, which is sensitive to particular chemical species which are to be detected by the sensor. The reaction of the sensitive layer with the chemical species to be detected results in a change in the physical properties of the sensitive layer, e.g. resistivity or surface potential. This change can be detected by monitoring the voltage signal across the sensitive layer. As the reaction of the sensitive layer is governed by thermodynamic relations, temperature plays an important role in optimising the output of the sensor device, e.g. sensitivity and selectivity.

Some sensors comprise a heater for increasing the temperature of the sensitive layer to increase the sensitivity and selectivity of the sensor. Depending on the chemical species to be detected, chemical sensors may need to be heated to quite high temperatures, for example in the range of 250°–650° C. With semiconductor sensors formed using thin film technology, the heater typically comprises a poly resistor which is compatible with the thin film technology. It is also known to use platinum wire heaters but such heaters are incompatible with CMOS processes. The heater is generally placed in the middle of the sensitive layer to reduce power consumption. The geometry of the heater can have an affect on the temperature homogeneity over the sensitive layer and hence the selectivity of the sensor.

It is known to form a poly heater having a S-shape with the heater contacts at each end of the 'S'. However, such a heater provides poor temperature homogeneity over the sensitive layer (about 40%). Moreover, the heater contacts are at a high temperature which can lead to silicon migration into the metal contacts. Silicon migration can change the resistance of the heater contacts which has the effect of causing a drift in the baseline of the sensitive layer; that is, the level of the voltage signal across the sensitive layer when there are no chemical species present changes.

An article entitled 'SI Planar Pellistor/Designs for Temperature Modulated Operation', written by Robert Aigner, Markus Dietl, Rainer Katterloher, Veit Klee and published in the Lehrstuhl fur Technische Elektronik, Technische Universitat Munchen, describes a spiral-shaped heater formed from platinum wire. This heater arrangement has improved homogeneity but is not compatible with CMOS processes. Furthermore, the heater can suffer from hot spots at the heater contacts which can lead to silicon migration as discussed above. If the spiral shape were to be applied to a poly resistor heater, the resistance of such a heater would be very high. Such a heater would therefore require a high supply voltage which would be too high for most applications where a supply voltage of less than 5 volts is required.

U.S. Pat. No. 5,345,213 discloses a chemical sensor having a concertina-shaped heater and a conductive heat distribution plate formed over the heater to act as a heatsink. The conductive heat distribution plate evenly distributes the heat from the heater so as to provide good temperature homogeneity over the sensor's sensitive layer. However, this arrangement does not completely avoid hot spots and since it requires two additional photo and deposition steps, is a more complex solution.

It is therefore desirable to provide an improved heater for a semiconductor chemical sensor device in which the above problems are mitigated.

SUMMARY OF THE INVENTION

In accordance with a first aspect of the present invention there is provided a semiconductor chemical sensor device comprising:

a semiconductor base;

a heater formed over the semiconductor base from conductive material, the heater comprising first and second arms extending over the semiconductor base from a heater portion and an opening extending vertically through the heater portion;

a first heater contact coupled to an end of the first arm;

a second heater contact coupled to an end of the second arm; and a sensitive layer for detecting specific chemicals, the sensitive layer being formed over the opening and heater portion, wherein a vertical axis through the center of the opening extends through the center of the sensitive layer.

The heater in accordance with the invention provides a substantially uniform temperature over the sensitive layer and ensures a low temperature at the heater contacts.

In accordance with a second aspect of the present invention there is provided a method of forming a semiconductor chemical sensor device comprising the steps of:

providing a semiconductor base;

forming a layer of conductive material over the semiconductor base;

patterning and etching the layer of conductive material to form a heater, the heater comprising first and second arms extending over the semiconductor base from a heater portion and an opening extending vertically through the heater portion;

forming an insulating layer over the heater;

forming a sensitive layer, for detecting specific chemicals, over the insulating layer so that it extends over the heater portion and opening, wherein a vertical axis through the center of the opening extends through the center of the sensitive layer;

forming first and second openings in the insulating layer, the first opening extending to an end of the first arm and the second opening extending to an end of the second arm; and depositing metal in the first and second openings to provide first and second heater contacts respectively.

BRIEF DESCRIPTION OF THE DRAWINGS

A semiconductor device in accordance with the present invention and a method of forming such a device will now be described, by way of example only, with reference to the accompanying drawings in which.

DETAILED DESCRIPTION OF THE DRAWINGS

Figure 1:
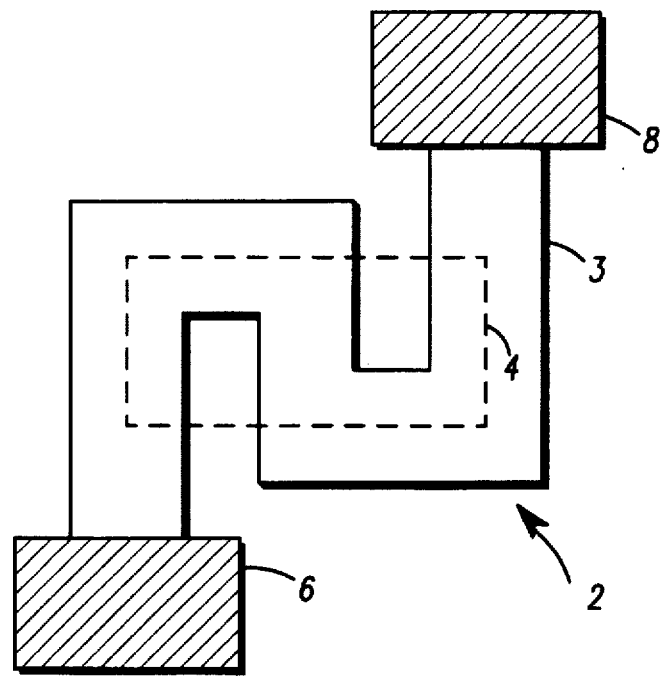
FIG. 1 is an enlarged simplified diagram of a top plan view of a known heater.

FIG. 1 shows a top plan view of the known S-shape heater 2 mentioned above, which heater 2 is used to heat a sensitive layer 4 of a chemical sensor device. The heater 2 comprises a heater portion 3 formed from polysilicon material shaped in an S and two metal contacts 6 and 8 at the respective ends of the S. The sensitive layer 4 is formed over a significant part of the heater portion 3.

Heater 2 suffers from a number of problems. In view of the shape of the heater portion 3, heater 2 provides a uniform temperature over only 40% of the area of the sensitive layer 4. Such poor temperature homogeneity results in poor sensor sensitivity. Another problem with this type of heater 2 is that the metal contacts 6 and 8 are, in use, at high temperatures which can lead to silicon migration into the metal contacts.

The present invention provides a heater which overcomes or at least mitigates these prior art problems.

Figure 2:
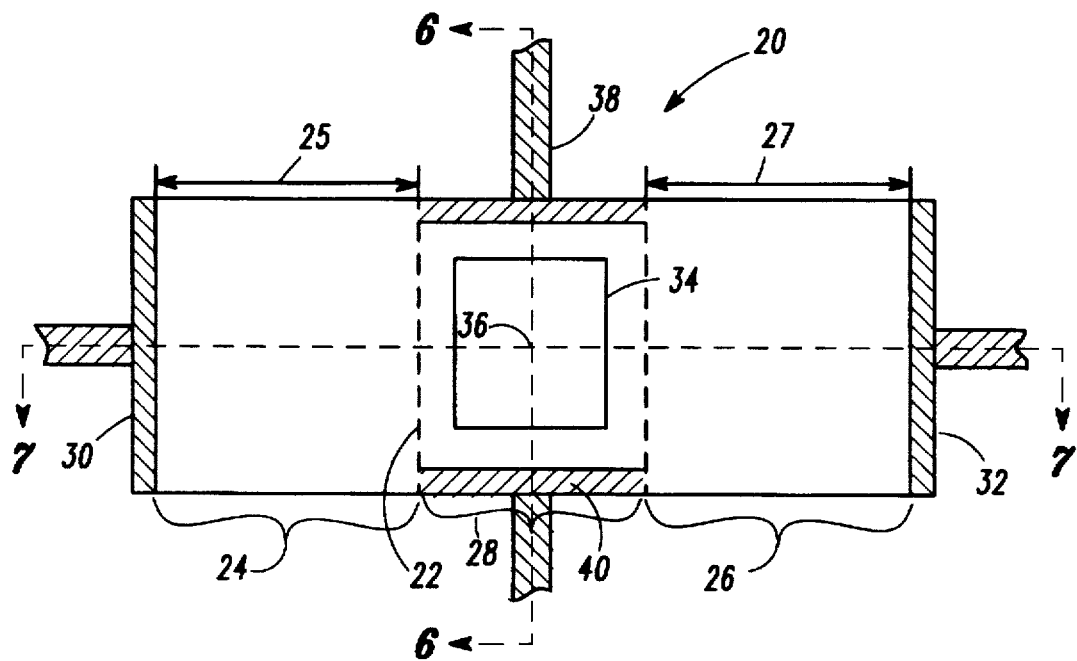
FIG. 2 is an enlarged simplified diagram of a top plan view of part of a semiconductor chemical sensor device in accordance with the present invention.

Referring now to FIG. 2, a top plan view of part of a semiconductor chemical sensor device 50 in accordance with the present invention is shown. The semiconductor chemical sensor device 50 comprises a heater 20 in accordance with a preferred embodiment of the present invention for use in heating a sensitive layer 22. The heater 20 is formed over a semiconductor base (not shown) from conductive material, which in the preferred embodiment is polysilicon material. The heater 20 comprises first 24 and second 26 arms and a heater portion 28. The first arm 24 and second arm 26 extend over the semiconductor base (not shown) from the heater portion 28. A first heater contact 30 is coupled to the end of the first arm 24 and a second heater contact 32 is coupled to the end of the second arm 26.

The heater 20 further comprises an opening 34 extending vertically through the heater portion 28. The sensitive layer 22 is formed over the opening 34 and heater portion 28 and the sensitive layer 22 and opening 34 are arranged such that a vertical axis through the center 36 of the opening 34 extends through the center 36 of the sensitive layer 22. Contacts 38 and 40 are coupled to two opposing ends of the sensitive layer 22. The voltage signal across the contacts 38 and 40 provides an indication of the presence of specific chemicals.

The opening 34 has a horizontal cross-section which has a symmetrical shape about the vertical axis through the center 36. The opening 34 enlarges the temperature distribution across the sensitive layer 22 in all directions perpendicular to the vertical axis. Since the opening 34 is symmetrical about the vertical axis and the centers 36 of the opening and sensitive layer 22 coincide, the temperature distribution is substantially even over the sensitive layer 22. Preferably, the center of the heater portion 28 is aligned with the centers of the opening 34 and sensitive layer 22 along the vertical axis.

The first arm 24 extends a first length 25 in one direction from the heater portion 28 to the first heater contact 30 and the second arm extends a second length 27 from the heater portion 28 in a substantially opposite direction to the one direction to the second heater contact 32. Each of the first and second lengths is greater than 100 microns.

Preferably, the first 24 and second 26 arms both have rectangular horizontal cross-sections. The lengths of the cross-sections of the first 24 and second 26 arms are the first and second lengths respectively and the widths of the cross-sections are equal. Since the heater contacts 30 and 32 are coupled to the heater portion 28 via the first 24 and second 26 arms, the temperature at the heater contacts 30 and 32 is reduced. The reduction in temperature depends on the first 25 and second 27 lengths of the first 24 and second 26 arms respectively. In the preferred embodiment, the first and second lengths are the same at 200 microns. The first 24 and second 26 arms thus reduce the problems due to hot spots and silicon migration.

The heater portion 28 preferably has a square-shaped horizontal cross-section having a width equal to the widths of the first and second arms. A square-shaped heater portion 28 and rectangular-shaped first 24 and second 26 arms means that the heater 20 has a low resistance which ensures that a low supply voltage (less than 5 volts) can be used to supply the heater 20. The heater portion 28 may however be a rectangular shape or any other shape that has a low resistance.

Figure 3:
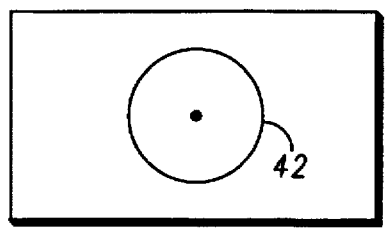
FIG. 3 is an enlarged simplified diagram of an opening of the heater in accordance with the present invention having a circular horizontal cross-section.
Figure 4:
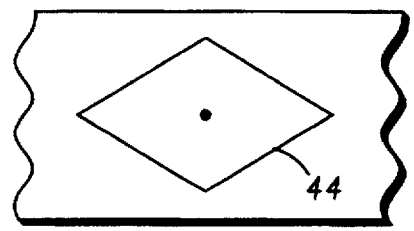
FIG. 4 is an enlarged simplified diagram of an opening of the heater in accordance with the present invention having a rhombus-shaped horizontal cross-section.
Figure 5:
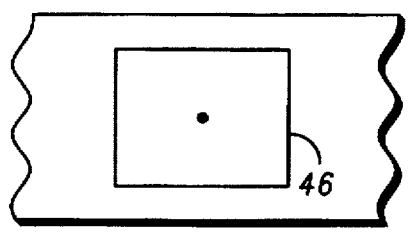
FIG. 5 is an enlarged simplified diagram of an opening of the heater in accordance with the present invention having a square-shaped horizontal cross-section with round corners.

In FIG. 2, the opening 34 is shown having a square-shaped horizontal cross-section. However, the opening's horizontal cross-section may take other shapes like those shown for example in FIGS. 3–5. FIG. 3 shows an opening 42 having a circular horizontal cross-section. FIG. 4 shows an opening 44 having a rhombus-shaped horizontal cross-section. FIG. 5 shows an opening 46 having a square-shaped horizontal cross-section with round corners. Other possible shapes for the opening's horizontal cross-section include a hexagon-shaped, or a star-shaped or a dodecagon-shaped cross-section.

Figure 6:
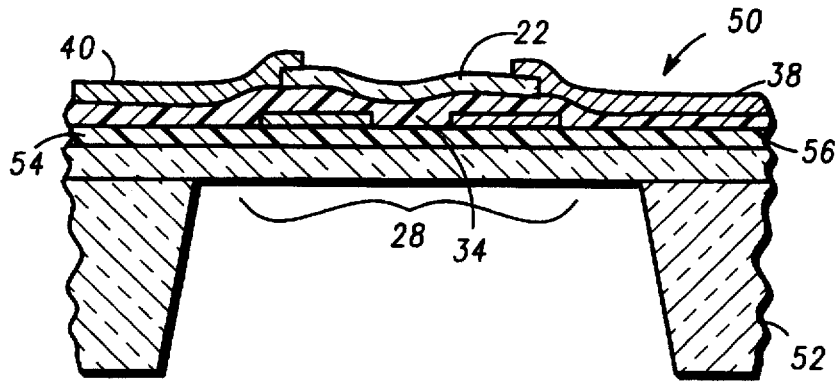
FIG. 6 is an enlarged simplified cross-section diagram of the semiconductor chemical sensor device of FIG. 2 along section line 6–6 and FIG. 7 is an enlarged simplified cross-section diagram of the semiconductor chemical sensor device of FIG. 2 along section line 7–7.

Referring now also to FIG. 6 which shows an enlarged cross-section view of the semiconductor chemical sensor device 50 of FIG. 2 along section line 6–6

The semiconductor chemical sensor device 50 comprises a semiconductor base 52 formed in a bridge and preferably of silicon material. A first insulating layer 54 is formed on the semiconductor base 52. A layer of conductive material is formed on the first insulating layer 54. The layer of conductive material is patterned and etched as is well known in the art to form the heater portion 28 having the opening 34 extending to the first insulating layer 54 and the first 24 and second 26 arms (not shown in FIG. 6) extending from the heater portion 28. A second insulating layer 56 is formed over the heater portion 28 and first insulating layer 54. A layer of sensitive material is formed over the second insulating layer 56 which layer is then patterned and etched to form the sensitive layer 22 over the heater portion 28. Metal is then deposited to form contacts 38, 40 to the sensitive layer 22.

In the preferred embodiment, the first insulating layer 54 is formed from silicon dioxide material and the second insulating layer 56 is formed from TEOS material. The type of sensitive material which is used to form the sensitive layer 22 may vary from metals to doped/compound materials and depends on the applications and the type of chemicals the semiconductor chemical sensor device is to detect. The sensitive layer 22 may be formed from a gold layer, or a gold-palladium alloy layer for sensing hydride gases. For a carbon monoxide sensor device, the sensing element 22 may comprise a tin oxide layer.

Figure 7:
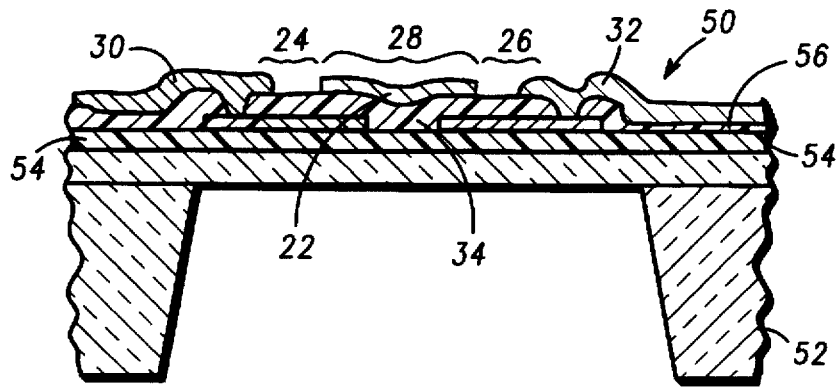

Referring now also to FIG. 7 which shows an enlarged cross-section view of the semiconductor chemical sensor device 50 of FIG. 2 along section line 7-7 The first 24 and second 26 arms are patterned and etched from the layer of conductive material as described above. The sensitive layer 22 is formed over the heater portion 28 and opening 34. Openings at the ends of the first 24 and second 26 arms are made in the second insulating layer 56 and metal is deposited therein to form the first 30 and second 32 heater contacts. The sensitive layer 22 may be formed before or after the contact openings are formed Thus, the semiconductor device in accordance with the present invention can be fabricated using known process steps and simply modifying the mask for the heater so that it produces a heater shaped in accordance with the present invention. It will therefore be appreciated that the semiconductor chemical sensor device in accordance with the present invention can be fabricated without the need for additional complex process steps.

In summary, the present invention provides a heater which provides improved temperature uniformity over the sensitive layer and which reduces the problems of poly/metal migration by reducing the temperature at the heater contacts. The heater portion has a low resistance shape which is preferably rectangular or square. The heater can be formed using well known processes and without the need for additional complex steps. The present invention is therefore compatible with CMOS processes.

Although the preferred embodiment of the invention has been described with reference to a semiconductor chemical sensor device, the heater in accordance with the present invention may be used in any semiconductor device which requires a heater to heat a layer.

We claim:

1. A semiconductor chemical sensor device comprising:
   a semiconductor base;
   a heater formed over the semiconductor base from conductive material, the heater comprising first and second arms, a heater portion having a first surface and an opposing second surface, and an opening extending vertically through the heater portion from the first surface to the second surface, wherein the first and second arms extend over the semiconductor base from the heater portion;
   a first heater contact coupled to an end of the first arm;
   a second heater contact coupled to an end of the second arm; and
   a sensitive layer for detecting specific chemicals, the sensitive layer being formed over the opening and heater portion, wherein a vertical axis through the center of the opening extends through the center of the sensitive layer and wherein the opening has a horizontal cross-section which has a symmetrical shape about the vertical axis.

2. A semiconductor chemical sensor device according to claim 1 wherein the horizontal cross-section of the opening has any one of the following shapes: a square, a circle, a rhombus, a square with round corners, and a rhombus with round corners.

3. A semiconductor chemical sensor device according to claim 1 wherein the center of the heater portion is aligned to the centers of the opening and sensitive layer along the vertical axis.

4. A semiconductor chemical sensor device according to claim 1 wherein the heater portion has a square-shaped horizontal cross-section.

5. A semiconductor chemical sensor device according to claim 1 wherein at least one of the first and second arms has a quadrilateral-shaped horizontal cross-section.

6. A semiconductor chemical sensor device according to claim 1 wherein the first and second arms have horizontal cross-sections having the same shape.

7. A semiconductor chemical sensor device according to claim 1 wherein the first arm extends a first length in one direction from the heater portion to the first heater contact and the second arm extends a second length from the heater portion in a substantially opposite direction to the one direction to the second heater contact, wherein each of the first and second lengths is greater than 100 microns.

8. A semiconductor chemical sensor device according to claim 7 wherein both the first and second arms have a rectangular-shaped horizontal cross-section, the length of the horizontal cross-section of the first arm being the first length, and the length of the horizontal cross-section of the second arm being the second length.

9. A semiconductor chemical sensor device according to claim 8 wherein each of the first and second lengths is 200 microns.

10. A semiconductor chemical sensor device according to claim 9 wherein the horizontal cross-sections of the first and second arms have the same width and the heater portion has a width which is perpendicular to the first and second lengths and is the same as the widths of the first and second arms.

11. A semiconductor chemical sensor device according to claim 1 wherein the heater is formed from polysilicon material.

12. A semiconductor device comprising:
    a semiconductor base;
    a heater formed over the semiconductor base from conductive material, the heater comprising first and second arms, a heater portion having a first surface and an opposing surface, and an opening extending vertically through the heater portion from the first surface to the second surface, wherein the first and second arms extend over the semiconductor base from the heater portion;
    a first heater contact coupled to an end of the first arm;
    a second heater contact coupled to an end of the second arm; and
    a layer for heating by the heater, the layer being formed over the opening and heater portion, wherein a vertical axis through the center of the opening extends through the center of the layer and wherein the opening has a horizontal cross-section which has a symmetrical shape about the vertical axis.

13. A semiconductor device according to claim 12 wherein the horizontal cross-section of the opening has any of the following shapes: a square, a circle, a rhombus, a square with round corners, and a rhombus with round corners.

14. A semiconductor device according to claim 12 wherein the center of the heater portion is aligned with the centers of the opening and layer along the vertical axis.

15. A semiconductor device according to claim 12 wherein the heater portion has a square-shaped horizontal cross-section.

16. A semiconductor device according to claim 12 wherein at least one of the first and second arms has a quadrilateral-shaped horizontal cross-section.

17. A semiconductor device according to claim 12 wherein the first and second arms have horizontal cross-sections having the same shape.

18. A semiconductor device claim 12 wherein the first arm extends a first length in one direction from the heater portion to the first heater contact and the second arm extends a second length from the heater portion in a substantially opposite direction to the one direction to the second heater contact, wherein each of the first and second lengths is greater than 100 microns.

19. A semiconductor device according to claim 18 wherein both the first and second arms have a rectangular-shaped horizontal cross-section, the length of the horizontal cross-section of the first arm being the first length, and the length of the horizontal cross-section of the second arm being the second length.

20. A semiconductor device according to claim 19 wherein each of the first and second lengths is 200 microns.

21. A semiconductor device according to claim 20 wherein the horizontal cross-sections of the first and second arms have the same width and the heater portion has a width which is perpendicular to the first and second lengths and is the same as the widths of the first and second arms.

22. A semiconductor device according to claim 12 wherein the heater is formed from polysilicon material.

* * * * *